United States Patent [19]

Dodge et al.

[11] Patent Number: 4,707,276
[45] Date of Patent: Nov. 17, 1987

[54] FLUID COLLECTION DEVICE WITH PHASE PARTITIONING MEANS

[75] Inventors: Larry H. Dodge, LaHabra, Calif.; Glen Stone, O'Fallon, Mo.

[73] Assignee: Sherwood Medical Company, St. Louis, Mo.

[21] Appl. No.: 485,757

[22] Filed: Apr. 22, 1983

Related U.S. Application Data

[63] Continuation of Ser. No. 254,555, Apr. 15, 1981, abandoned, which is a continuation of Ser. No. 31,816, Apr. 20, 1979, abandoned.

[51] Int. Cl.$^4$ .............................................. B01D 21/26
[52] U.S. Cl. .................................... 210/789; 210/511; 210/516
[58] Field of Search ............... 210/511, 514, 515, 516, 210/DIG. 24, 927, 789; 422/101, 102; 254/555

[56] References Cited

U.S. PATENT DOCUMENTS

| | | | |
|---|---|---|---|
| 3,852,194 | 12/1974 | Zine, Jr. ..................... | 210/DIG. 24 |
| 3,920,549 | 11/1975 | Gigliello et al. ............... | 210/516 X |
| 3,957,654 | 5/1976 | Ayres ................................ | 210/516 |
| 3,976,579 | 8/1976 | Bennett ............................. | 210/516 |
| 3,981,804 | 9/1976 | Gigliello ........................... | 210/516 |
| 3,997,442 | 12/1976 | Gigliello et al. ............... | 210/927 X |
| 4,021,340 | 5/1977 | Zine, Jr. .......................... | 210/515 X |
| 4,046,699 | 9/1977 | Zine, Jr. ........................... | 210/516 |
| 4,055,501 | 10/1977 | Cornell ............................. | 210/516 |
| 4,088,582 | 5/1978 | Murty et al. ..................... | 210/516 |
| 4,246,123 | 1/1981 | Cornell et al. ............. | 210/DIG. 24 X |

Primary Examiner—David Sadowski
Attorney, Agent, or Firm—Stanley N. Garber; Andrew J. Beck; William R. O'Meara

[57] ABSTRACT

A blood collection device is provided with a phase partitioning device which includes a standpipe connected to a reservoir filled with a sealant material having a specific gravity intermediate the specific gravities of separated light and heavy phases of blood. Components of the heavy phase of blood enter the reservoir during phase separation and centrifugation to force sealant upwardly in the standpipe and out into the tube above the line of separation.

10 Claims, 4 Drawing Figures

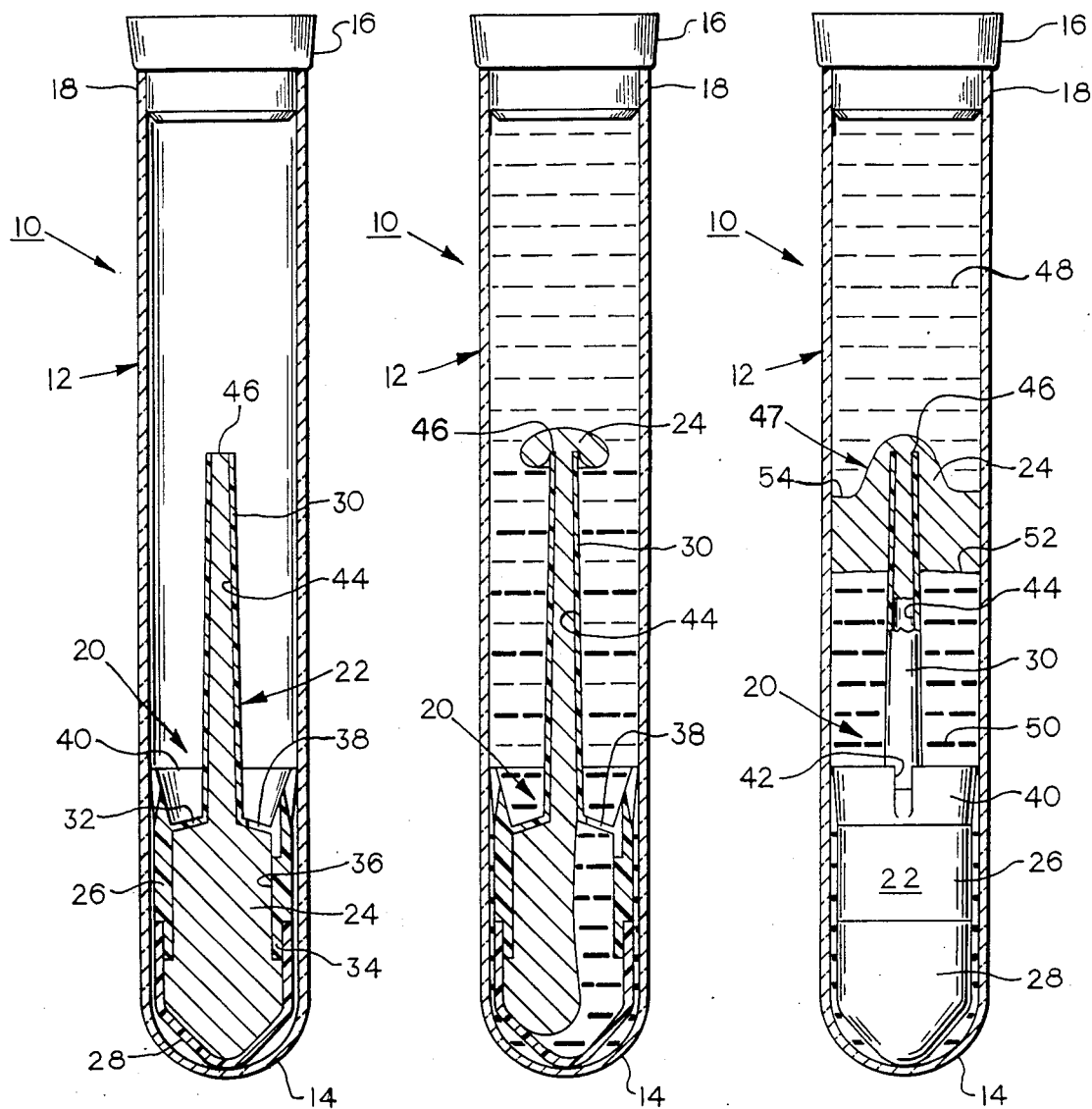
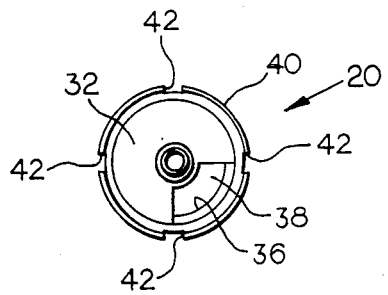
FIG. 2

FLUID COLLECTION DEVICE WITH PHASE PARTITIONING MEANS

This application is a continuation of application Ser. No. 254,555, filed Apr. 15, 1981, abandoned, a continuation of application Ser. No. 031,816, filed Apr. 20, 1979, abandoned.

BACKGROUND OF THE INVENTION

This invention relates to fluid collection devices, and more particularly, to blood collection devices having means for partitioning the relatively light phase from the relatively heavy phase.

When taking blood samples for test purposes, whole blood is generally drawn into an evacuated collection tube and the tube subsequently centrifuged to separate the blood into its relatively light phase, serum or plasma, and its heavier cellular phase. Blood phase separators or partitioning devices have been used to provide a partition or barrier between the separated phases until the light phase is removed for clinical testing. Many types of blood phase partitioning devices have been proposed, all with varying degrees of success. Some proposed partitioning arrangements include the use of a sealant or gel-like thixotropic material having a specific gravity intermediate the specific gravities of the light and heavy blood phases so that during centrifugation and phase separation the sealant flows to the interface of the two phases and forms a partition between them. Various gel-like thixotropic materials or sealants are now well known. For example, in U.S. Pat. No. 3,852,194, a mixture of silicone and hydrophobic silicon dioxide powders is used to form a partition between the separated phases. In U.S. Pat. Nos. 4,021,340; 4,088,582 and 4,055,501, mixtures including liquid polybutene polymer and silicon dioxide powders are used as phase partitioning materials.

A serious problem in utilizing such partitioning materials is that the partitioning barrier is sometimes formed too soon after centrifugation begins so that blood cells are trapped above the partitioning barrier in contact with the serum or plasma after phase separation. Such cells tend to contaminate the lighter phase to such a degree, in some cases, that certain test results are unreliable or inaccurate. Cells have been trapped in or above the partitioning barrier because the rising partitioning material engages descending cells and carries them to the interface of the two phases.

Also, in some cases, the separated serum was found to have excessive lactic dehydrogenase (LDH) which was believed to be caused by hemolysis of red cells due to the impact of the cells with the partitioning material under the influence of centrifugal forces. When this occurs, the test results are inaccurate since some of the LDH indicated is caused by the process, that is, due to centrifugal separation and partitioning of the phases.

SUMMARY OF THE INVENTION

Accordingly, it is an object of the present invention to provide a fluid collection device having partitioning means for forming a barrier between separated light and heavy phases of multi-phase liquid, such as whole blood, during centrifugation while avoiding or minimizing hemolysis of blood cells and blood cell contamination of the light phase. In accordance with one form of the present invention, a fluid collection device is provided with a sealant material, having a specific gravity between the specific gravities of the separated phases, disposed in a lower portion of a collection container. A standpipe having a passageway is provided for the flow of the sealant material during centrifugation upwardly from the lower portion of the container and out of the passageway at a point in the container that is above the upper level of the separated heavy phase.

These, as well as other objects and advantages of the present invention, will become apparent from the following detailed description and drawing.

BRIEF DESCRIPTION OF THE DRAWING

FIG. 1 is an elevational cross-sectional view of a blood collection container which includes a phase partitioning device in accordance with a preferred embodiment of the present invention;

FIG. 2 is a top plan view of the phase partitioning device of FIG. 1;

FIG. 3 is an elevational cross-sectional view of the collection container of FIG. 1 after blood has been drawn into it and while the device is being centrifuged to separate the blood phases; and FIG. 4 is an elevational cross-sectional view of the blood collection container of FIG. 1 after complete blood separation and centrifugation.

DESCRIPTION OF THE PREFERRED EMBODIMENT

Referring now to the drawings, and more particularly to FIG. 1, a blood collection device 10 is shown including a blood collection container or tube 12 having a lower end 14 formed integrally with the tube, a stopper 16 closing the upper end 18 of the tube, and a blood phase partitioning device 20 disposed within tube 12. Stopper 16 is made of a suitable rubber which is pierceable by a needle cannula for introducing a sample of blood into the tube, and is self-sealing when the needle cannula is removed. Tube 12 is preferable made of glass and is ajar evacuated to provide a negative pressure within the tube for facilitating the flow of blood into the tube.

The phase partitioning device 20 includes a hollow, generally cylindrical housing 22, and a gel-like sealant material 24, which will be discussed hereafter, that fills the housing 22. Housing 22 is shown including a sleeve 26 having an open lower end which is closed by a cup-shaped cap 28, and an upstanding tubular member of standpipe 30 coaxially connected to the sleeve 26 by a web 32. Cap 28 frictionally receives a sleeve portion 34 of reduced diameter so that the inner walls of the sleeve 26 and cap 28 form a chamber 36 serving as a reservoir for the gel or sealant 24. The web 32 has an opening 38 therethrough for permitting a portion of the heavy cellular phase to enter chamber 36 and displace sealant 24, as will be dicussed hereafter.

Sleeve 26 has a resilient, radially outwardly and upwardly flaring upper portion 40 which frictionally engages the inner sidewalls of tube 12. The resilient portion 40 allows the partitioning device 20 to be inserted into the tube during assembly and then holds it in place at the lower end of the tube during handling and use of the blood collection device. As seen also in FIG. 2, the resilient portion 40 is segmented by providing four circumferentially spaced slots 42.

The standpipe 30 provides a gel flow passage 44 which is open at its opposite ends. The lower end of passage 44 connects with the top of reservoir 36 while the upper end provides an outlet at the upper end 46 of the standpipe.

In the illustrated embodiment, the sleeve 26, standpipe 30, and web 32 are integrally formed, such as by molding a suitable plastic, for example, polyethylene or the like and may be formed of a material having a greater specific gravity than the heavy phase. The cap 28 may also be molded of similar material. After filling the partitioning device 20 with the gel 24, the device 10 may be assembled in a vacuum by first inserting the positioning device 20 into tube 12 and then inserting stopper 26 which will maintain the desired negative pressure in the tube.

The sealant 24 is a thixotropic gel-like material that is substantially water insoluable and inert to the components of blood and has a specific gravity intermediate the specific gravities of the separated light phase, serum or plasma, which is about 1.03, and the heavy cellular phase, which is about 1.09. Sealant 24 is preferably formed to having a specific gravity between 1.035 and 1.05. The sealant 24 at rest and under normal handling and shipping is semi-solid or non-flowable, but when subjected to forces, such as during centrifugal separation of blood phases, becomes flowable. Upon cessation of centrifugal forces the sealant returns to its non-flowable state. Sealant 24 may be a mixture of silicone and silicon dioxide powders or a mixture of liquid polybutene polymer and silicon dioxide powders, as previously mentioned herein.

One specific example of a useful sealant is described in U.S. Pat. No. 4,088,582, and includes 100 parts by weight of liquid polybutene (Polybutene Grade 24 - Chevron Chemical Company of San Francisco, Calif.), 20 parts by weight of hydrophillic silica powder (Min-U-Sil 10, PGS, a subsidiary of ITT, Pittsburgh, Pa.), and 9 parts by weight of a hydrophobic silica powder (aerosil R-972, Degussa Inc., Pigments Division, New York, N.Y.). The latter silica powder was made hydrophobic by a process including flame hydrolysis of silica, and then reacting the silica with dimethyl dichlorosilane and steam. By varying the proportions of polybutene and silica powders desired viscosity and specific gravity characteristics can be obtained.

A sample of blood may be drawn into the blood collection device 10 by use of a double-ended needle cannula, such as provided by a conventional needle holder and tube guide (not shown). For example, after the distal end of the cannula is inserted into the vein of a patient, the device 10 is moved onto the proximal end of the cannula until the cannula pierces stopper 16, whereupon whole blood flows into tube 12. The filled tube is subsequently placed in a centrifuge such that the lower end 14 will be radially outwardly of the stopper and axis of rotation of the centrifuge during centrifugation. As is well known, if it is desired to separate serum, a blood clot is formed before centrifuging the filled tube.

During centrifugation, blood cells and other components of the heavy cellular phase move downwardly toward the lower end 14 of tube 12, while the light phase moves toward the upper end 18. The portions of the heavy cellular phase are forced into opening 38 of the housing 22 of the partitioning device and displace sealant material 24 causing sealant to move upwardly in passage 44 and out the upper end 46 of the standpipe 30, as illustrated in FIG. 3. As centrifugation proceeds the cellular phase continues to displace the sealant from the reservoir 36 causing it to flow upwardly in standpipe 30. Because the sealant 24 has a specific gravity between the specific gravities of the lighter and heavier phases, it seeks the interface between the separated phases during centrifugation. After complete phase separation and centrifugation, the sealant provides a liquid impervious, substantially non-flowable, barrier or partition between the two separated phases as illustrated in FIG. 4. The separated light phase, serum or plasma, is indicated at 48 and the heavy cellular phase at 50.

The standpipe 30 is made long enough so that the upper open end 46 of the passage 44 when in collection tube 12 will be above the upper surface, indicated at 52 in FIG. 4, of the separated cellular phase 50, and preferably above the upper surface 54 of the main portion of the sealant 24 when it forms the partition 47. Because of the length of standpipe 30 and the relative specific gravities of the sealant 24 and blood phases, some of the sealant 24 will remain in the upper portion of the standpipe 30 to seal off blood cells in member 22 from the lighter phase 48.

Because of the inertia of the sealant 24 and because it must pass through the relatively narrow passage 44, flow of the sealant is metered so that formation of the partition or barrier is delayed to thereby allow time for phase separation to occur. By having the sealant issue from the standpipe 30 at a point or location in tube 12 above the highest expected level 52 of the cellular phase, the sealant issues from standpipe 30 and moves downwardly or toward tube end 14 as the partition is forming during centrifugation. Thus, the sealant 24 will tend to cover any blood cells that might remain on the first or lower portions of the partition 47. The flow rate of the sealant, which is affected mainly by the specific gravity and viscosity of the sealant, and the minimum diameter or cross-sectional area of the passage 44, is preferably such that all or substantially all of the blood cells have passed by the upper end 46 of the standpipe 30 before the sealant flows from the standpipe. This tends to prevent trapping cells in the light phase and ensures that substantially all of the cells will be sealed from the light phase 48 after complete phase separation to thereby provide a high quality sample from which accurate test results can be obtained.

Since the sealant 24 flows upwardly within standpipe 30 while passing through a lower portion of the collection tube during phase separation, there is substantially less engagement between ascending sealant and descending cells and less cells being carried to the interface than there would be without the standpipe. This tends to result in less blood cell hemolysis and less artificial LDH being introduced into the sample due to the phase separation process.

One desirable construction using a 16×127 mm tube, a 85% draw (12.2 ml), 1 cm (1.5 ml) barrier height, and effective for hematocrits up to about 50%, may employ a partitioning device having a height of about 7.7 cm. The inner diameter of the standpipe may taper, for example, from about 3.1 mm at the bottom to about 1.9 mm at the top.

As various changes could be made in the above construction without departing from the scope of the invention, it is intended that all matter contained in the above description or shown in the accompanying drawing shall be interpreted as illustrative and not in a limiting sense.

What is claimed is:

1. A fluid collection device for receiving whole blood separable into relatively light and heavy phases during centrifugation of the device comprising a glass container for receiving the blood and having interconnected upper and lower container portions for containing the separated relatively light and heavy phases, respectively, after separation thereof, said container having a closed, integral, glass bottom end and an opposed open upper end, a stopper closing said upper end and pierceable by a needle for introducing blood into said container, and phase partitioning means in said container including a thixotropic gel-like sealant material in an initial location in said lower container portion at said bottom end and having a specific gravity intermediate the specific gravities of the separated light and heavy phases, said sealant material being closer to said bottom end than to said upper open end and flowable from said initial location in an upward direction toward said stopper during phase separation to a final location to provide a partition between the separated phases after phase separation, and elongated passage means disposed in stationary relation with respect to said container during phase separation and centrifugation of the device and having a lower passage portion in said lower container portion in fluid communication with said sealant material and an upper passage portion with a sealant outlet spaced upwardly from said lower passage portion and disposed within said upper container portion for passing said sealant material during centrifugation of the device upwardly from said initial location through said lower container portion to said upper container portion, said sealant material in said lower container portion being displacable upwardly in said passage means during centrifugation of the device by blood components in said lower container portion.

2. The device of claim 1 wherein said container normally has an internal negative pressure therein.

3. The device of claim 1, wherein said pipe is sized to restrict the flow of said sealant therethrough to delay completion of the formation of said partition until substantially complete phase separation has occurred.

4. The device of claim 1 further including sleeve means in said container connected to said lower passage portion with at least a portion of said sealant within said sleeve, said lower container portion having inner walls engaged by said sleeve means.

5. The device of claim 1 further including a chamber connected to said lower passage portion and having at least a portion of said sealant therein, said lower container portion having inner wall surfaces engaging said chamber, and said chamber having an opening therein for the flow of blood components of the heavy phase therethrough.

6. The device of claim 1 wherein said partitioning means comprises a chamber and said passage means comprises a standpipe having its lower end in fluid communication with said chamber, said sealant material is disposed in said chamber and said standpipe, and said chamber has an opening for the flow of blood components therethrough for displacing said sealant material as it flows upwardly in said standpipe during phase separation.

7. The device of claim 6 wherein said container has an inner sidewall, and said phase partitioning means frictionally engages said inner sidewall to resist relative movement therewith.

8. The device of claim 6 wherein said material has a specific gravity between about 1.03 and about 1.06.

9. The device of claim 6 wherein said chamber and said passage means define a housing having a specific gravity greater than that of the separated heavy phase.

10. A method of separating whole blood into its lower density and higher density phases and providing a partition between the separated phases comprising the steps of utilizing a glass blood collection container having a chamber in the lower end portion of the container and which contains a thixotropic gel-like sealant material having a specific gravity between those of the lower and higher density phases, the container having an upper end closed by a stopper and a closed, integral, glass bottom end, said chamber having a standpipe connected thereto and in communication with the sealant and having an outlet spaced from the chamber and disposed in that portion of the container that is above the upper level of the higher density phase when separated from the lower density phase, said chamber and initially the sealant material therein being at the bottom end of the container closer to the bottom end than to the upper end of the container and in fluid communication with the lower end portion of the container before centrifugation, introducing whole blood into the container through a needle piercing the stopper, centrifuging the container with the blood therein so that the higher density phase separates to the lower end portion of the container and simultaneously urges sealant from the chamber upwardly through the standpipe and through the outlet into the container and then downwardly from the outlet to form a partition, maintaining the chamber and standpipe stationary with respect to the container during phase separation and centrifugation, and continuing centrifugation of the container at least until the phases are completely separated and the sealant provides a partition between the separated phases.

* * * * *